US00PP17329P3

(12) United States Plant Patent
Saville

(10) Patent No.: US PP17,329 P3
(45) Date of Patent: Jan. 2, 2007

(54) MINIATURE ROSE PLANT NAMED 'SAVAPAM'

(50) Latin Name: *Rosa chinensis hybrida*
Varietal Denomination: SAVapam

(76) Inventor: John Saville, 48 Carter St., Newburyport, MA (US) 01950

( * ) Notice: Subject to any disclaimer, the term of this patent is extended or adjusted under 35 U.S.C. 154(b) by 58 days.

(21) Appl. No.: 11/096,569

(22) Filed: Apr. 1, 2005

(65) Prior Publication Data

US 2006/0225166 P1 Oct. 5, 2006

(51) Int. Cl.
*A01H 5/00* (2006.01)

(52) U.S. Cl. ..... Plt./128

(58) Field of Classification Search ..... Plt./116, Plt./121, 122, 123, 128, 129, 107
See application file for complete search history.

(56) References Cited

U.S. PATENT DOCUMENTS

PP5,097 P * 9/1983 Saville ..... Plt./121

* cited by examiner

*Primary Examiner*—Howard J. Locker

(57) ABSTRACT

'SAVapam' is a new and distinct variety of miniflora rose plant primarily identified by its double, old-fashioned, pink and pink blend flowers on an upright and well branched plant. Flowers last a long time both on the plant and as cut flowers. Its dark green, semi-glossy foliage has shown exceptional disease resistance in national, outside testing. 'SAVapam' is hardy as least to zone 5 and heat tolerant at least to zone 9.

1 Drawing Sheet

CROSS REFERENCE

The present invention can be compared to 'SAVahowdy' (U.S. Plant Pat. No. 5,097), which is from this same hybridizing program. The coloring of the flowers of both cultivars has a darker pink splashed onto the lighter pink of the outer petals. The flowers of these two plants have similar petal counts and similar thickness and texture to the petals. Both cultivars have above average disease resistance.

Similarities may also be seen between this new invention and a miniature rose named 'Kay Denise' (U.S. Plant Pat. No. 10,946). Although 'Kay Denise' is overall slightly smaller the flowers take on a similar appearance to that of this new invention, especially during the warmer months.

These three plants are related through the rose variety 'Little Darling' (U.S. Plant Pat. No. 1,581,), a light yellow and pink blend floribunda. 'Little Darling' is a grandparent to both this new cultivar and 'SAVahowdy' and a great-grandparent to 'Kay Denise'.

These roses may be differentiated by flower and foliage size and plant habit. The new invention has a larger open bloom and larger foliage than either 'SAVahowdy' or 'Kay Denise' and grows 10 to 12 inches taller either, which is why this new cultivar, 'SAVapam', is classified as a miniflora. Although the open bloom is of similar size to the open blooms of 'Little Darling', the individual petals are not as broad on the new invention and the plant of the new invention is somewhat smaller, with shorter internodes and slightly smaller foliage.

Genus and species: This present invention relates is a new variety of *Rosa chinensis hybrida.*

Varietal denomination: This new cultivar has the varietal denomination of 'SAVapam'.

BACKGROUND OF THE INVENTION

This new and distinct variety of miniflora rose was created under controlled conditions in a greenhouse in Rowley, Mass., in 1994, by crossing 'MORpoly' (U.S. Plant Pat. No. 8,453) as the seed parent with pollen from 'MACgenev' (U.S. Plant Pat. No. 8,279). Goals of this breeding program include disease resistance and hardiness along with fragrance and hybrid tea type, exhibition form in diminutive size roses. In an attempt to breed toward this end, 'MORpoly' was selected for its diminutive size and 'MACgenev' was selected for its flower form and fragrance. Both parent plants are known for their vigor, hardiness and above average disease resistance. Over a consecutive two year period in this hybridizing program, over 7,000 seeds were planted from this cross in a controlled environment. Germination rate was 30 to 40 present. A total of 65 plants were chosen for further evaluation. Only two of those seedlings were classified as pink blends, one of them being this new cultivar, 'SAVapam'. Two other roses were previously introduced from this line, 'SAVyk' (U.S. Plant patent application Ser. No. 09/731,482, abandoned) and 'SAVanade' (U.S. Plant Pat. No. 11,810), both being dark yellow miniatures, with good vigor and above average disease resistance, and neither having notable fragrance.

While the new cultivar does not have strong fragrance or hybrid tea form flower form, it did prove to be highly resistant to diseases and insects and is very winter hardy. The flower size is larger than the typical miniature but fits well into the newer classification of miniflora. The flower form is more typical of an old-fashioned flower. The old-fashioned flower form and its vigor and larger size make it a very marketable plant.

Similarities with the seed parent, 'MORpoly' are not obviously apparent. Both the seed parent and the new cultivar are vigorous and well branched. The thickness, texture and appearance of the flower petals are the same. Seedlings from this seed parent often have the increased disease resistance found in this new cultivar.

The most immediate difference is flower color and form—'MORpoly' is all yellow with near hybrid tea form while the new cultivar is only yellow near the base of the petals and has an informal, old-fashioned form.

This new cultivar has similarities to its pollen parent, 'MACgenev', with similar flower coloring and petal counts. The differences between the two are most noticeably in the sizes of the flowers and plants. 'MACgenev' is an hybrid tea with much larger flowers and plant habit.

BRIEF SUMMARY OF THE INVENTION

The Present invention relates to a new and distinct variety of hardy, dwarf, bush-type rose plant of the miniflora class. Among the characteristics which distinguish this new invention from others presently available, of which I am aware, are its unique combination of the following: the shade of pink coloring of the petals on a plant of miniflora size; its double, old-fashioned, cupped bloom form; flowers that open slowly and with great substance, lasting 2 weeks or more on the plant or as cut flowers; its blooms are born mostly solitarily; its mild degree of fragrance; its above average disease resistance; its degree of winter hardiness as well as its degree of heat tolerance.

Other notable characteristics are its semi-glossy, dark green foliage on a full, upright, well-rounded and well-branched plant with abundant and near continues bloom production, making it very suitable for outdoor decoration.

Successive asexual reproduction by cuttings of this new variety in Rowley, Mass., and Arroyo Grande, Calif., have shown that all distinguishing characteristics of this rose continually come true to form.

BRIEF DESCRIPTION OF THE DRAWING

The accompanying color photographs show specimens of this new cultivar in different stages of development, from plants grown in San Luis Obispo County, in California. The flowers in the larger picture are from plants grown in a greenhouse where the top is opened in good weather, allowing for direct sunlight to hit the plants. The flowers in the inset are from plants that were grown under plastic. The sunlight directly on the plants created the greater intensity and variations of color, as seen in the larger image.

BOTANICAL DESCRIPTION OF THE PLANT

The following observations, measurements, values and comparisons describe plants of this new invention, 'SAVapam'. at 6 or more years of age growing outdoors in Essex County, Mass., in standard, 8-inch nursery containers, in an artificial soil mixture with intermittent liquid feed. Past observations have noted soil pH, nutrition and various light intensities directly affect the intensity and degree of color found in and on the bloom and foliage. On plants grown outside, the cooler temperature of fall create the most intense color and variegation. Low pH and accompanying low nutrient levels allow for considerably less color variegations and a much paler color in both the flowers and the foliage. The flower form and general color and plant habit still allow the plant to be clearly identified as 'SAVapam'. For this written botanical description, the plants observed had good pH and nutrient levels, throughout the summer months. Throughout this specification, color references are to The Royal Horticultural Society Colour Chart except where common terms of color definition are employed.

Parents: 'MORpoly' by 'MACgenev'.
Botanical classification: *Rosa chinensis hybrida.*
Commercial class: Miniflora.

FLOWERS

The new cultivar usually bears its flowers singly but may also be in pyramidal clusters of three to five, especially on those flowering stems originating near the base of the plant in candelabra-type growth.

Outdoors, the plant is a recurrent bloomer with a very short time between bloom cycles. Under greenhouse conditions, the plants can easily be kept in continual bloom. The flowers are a blend of pinks and corals and have moderate fragrance.

Buds: The size of the buds, just before the sepals first divide, varies from 17/32 to 21/32-inch long and from 7/16 to 9/16-inch wide at the widest point. The most common size is 21/32-inch long and 15/32-inch wide with the shape of ovoid with a cuspidate apex and truncate base. The color when the sepals first divide is rhodonite red, near 51A.

Sepals: As the flower opens, the sepals most often roll back to become perpendicular to the stem, sometimes with the outer ends curling up or down and often with involute margins, and remaining in that position, attached to the receptacle, until after the hips ripen. The color of the outer surface is 146B, sometimes with weak anthocyanin coloration present, and becoming near 144A at the center and base of each sepal. The sepals are elliptical, starting from the truncate base at their attachment to the receptacle, becoming penicullate and with the outer 3 sepals having a lanceolate tip that is one-fourth to one-third of the entire length of the entire sepal. Sepals extend 5/16-inch beyond the tip of the bud, just before they start to divide. All five sepals are 5/16-inch wide at their widest point. Inside texture is tomentose, appearing a light green, near 148C.

The two innermost sepals have ciliate margins but no foliar appendages and are 12/16- to 14/16-inch long. The outer surfaces have hairs decreasing from the ciliate margin to one-third of the distance in from the margin to the center, being void of hairs in the center.

The two innermost sepals are 14/16- to 17/16 inch long. Margins are ciliate with one or two linear-shaped appendages on each margin and stipitate glands, near evenly spaced at the rate of approximately one every 1/32-inch, but none along the margin of the lanceolate portion at the tip. The outer surfaces have only a few random hairs. The linear appendages are void of hairs on both surfaces. Looking down on the adaxial side of these sepals, near the base of the linear appendages on the right side of the sepal, there is a stipitate gland. There are usually no stipitate glands at the base of the linear appendages along the left side of the sepals.

The one sepal in-between the two outer and two inner sepals is a perfect combination of both, with only one margin having a linear appendage and the outer surface having one-half the same as that of the inner sepals and one-half the same as the outer sepals.

Peduncle: The length of the peduncle varies from 3/4-inch to 1 1/4-inch, being most often either 1- or 1 1/4-inch long, standing straight and strong. The width is consistently 3/32 inch. The surface has minute prickles and stipitate glands. The color is a medium green, near 145B, with reddish-anthocyanin coloring weak or absent. A three-leaflet leaf and/or stipule-like appendage is at the base of the peduncle.

Receptacle: The receptacle is smooth, glossy and glabrous with a medium yellow-green color, near 144A. The diameter is 8/32 to 13/32 inch with a conical or cuneate profile, being truncate at the top. The stop surface is lighter, near 145D, and circular with a diameter varying from 8/32- to 13/32-inch but 13/32-inch is the most common diameter during the warmer months. An alveoli centered in the top most often measures 5/32-inch in diameter.

Bloom: When fully expanded the bloom measures 2½- to 3-inches across and 15/16-inch to 1 1/16-inch deep. The upper profile is flat from opening to fade. The lower profile starts cupped and then becomes flattened with petals slightly revolute. During the warmer summer months petalage averages 28, ranging from 27 to 32 with 2 to 8 petaloids but exceeds 50 petals plus petaloids during the first blooms of spring.

Petals: Petals are imbricated. Petals are thick and moderately heavy. Both surfaces appear satiny. Upper surface texture is slightly rugose and glabrous; the reverse is generally glabrous and smooth, being slightly rugose near the outer margin where it begins to curl under. Where there is white streaking on the upper surface of the three outer petals, the center most portion of the white is tomentose.

The width of the outermost petals is ⅞-inch and the length is 15/16- to 1 1/16-inches long. The shape of the three outermost petals is broadly cordate. The remainder of the outer petals are broadly obtuse or fan shaped. Progressing in toward the center of the flower, the form of the petals graduates to obovate-rotundate, then to obovate-oblong and finally to oblong for the innermost petals and petaloids. The outer margins are generally lunate and are often cleft or deeply notched on either side of an acute apex, but may only be slightly indented on one or equidistant on both sides of the apex. The outer petals are most apt to be deeply indented on one side of apex. The innermost petals and petaloids become increasingly lobed with margins becoming crenate and ruffled closest to the center. Some petaloids have truncate upper margins and/or are only the left or right five-sixths of a petal.

Color newly opened flower: Right after the sepals divide, along the outer margins of the the three outermost petals where they were first exposed to the sun, is rhodonite red, near 51A. The rest of the upper surface is shell pink, near 37C, blending into an empire rose, near 48D, and a light yellow, near 2B, at attachment. There is often a white streak, near 155B, that may branch out into the petal. The reverse of only the two outermost petals have a cuneate patch of rhodonite red on or near the central vein where the petals were first exposed to the sun by the dividing sepals. The surface on either side of that patch and along the upper margin is much lighter, near 54D, spinel red. The remainder of the surface appears shell pink, near 37D, as it blends in with carrot red, near 29C, at the base and near 2C at attachment.

As the bloom opens somewhat, the inner petals at the center of the flower are an orient pink, near 36A, on their upper surface which blends into mimosa yellow, near 8C, becoming near 8A at attachment. The reverse is orient pink, near 36C, on the upper one-third, then blending into mimosa yellow, near 8B, from the base and point of attachment. The outer petals become rhodonite red, near 51D, around the margins, lightening slightly as two-thirds of the way down the petal, it blends into a primrose yellow, near 9A, from the base and point of attachment. The reverse becomes near 51D for the upper third before it starts blending in with chartreuse yellow, near 2B, from the base and the cuneate streaking still appearing near 51A. The point of attachment is a chartreuse green, near 145B.

Color of full open flower (5 to 8 days): The color of the outer petals lightens somewhat to shell pink, near 37D, and blends in with mimosa yellow, near 8C from the base and aureolin, near 12A, at attachment. The reverse becomes orient pink, near 36B and then appears as if flushed by the 48D towards the base, and Naples yellow, near 11B, at the point of attachment. The upper surface of the inner petals becomes a medium yellow to light yellow, near 159C, for their upper half and Indian yellow, near 19C, for the lower third and blending in-between, and lemon yellow, near 14B, at attachment. The reverse is peach, near 29D, and becoming salmon, near 27A, towards the base and Naples yellow, near 11B, at attachment. The color of the petaloids is similar to that of the outermost petals, occasionally having a streak of Naples yellow, near 11B, from the point of attachment up the central vein on their reverse.

Blooms may fade to uniformly light peach, near 29D or lighter before the petals begin to drop cleanly from the plant. This entire process may take 5 to 8 days to fully opened bloom from when the sepals reflex and an additional 5 to 7 days in the fully opened stage, before the bloom begins to fade. Cut flowers can last 10 to 14 days or longer.

REPRODUCTIVE ORGANS

Stamens filaments and anthers are regularly attached along the upper perimeter of the receptacle, adjacent to the petals and are 75 to 100 in number, with the greater quantity being during the warmer months. Filaments are up to ¼-inch long and a lemon yellow, near 14C. The anthers are a very pale yellow, near 19D, with abundant pollen of a deep orange-yellow, near 20A.

Pistils are located in an alveola in the center of the receptacle. They are about sixty percent fewer in number than the stamens. Styles are very thin and very undulate, varying between 2/16- and 3/16-inch long. Their color is a translucent shade of Tyrian purple, near 61C, and the stigmas are French rose, near 49D. Stigmas are very receptive to many different rose pollens.

This new cultivar readily sets hips and will self-pollinate. The hips are indehiscent. Their shape varies from pyriform to ovato-rotundo. The surface is smooth and glabrous. Seeds do not usually protrude. Diameter of the hips can vary from 9/16- to 11/16-inch.

PLANT

The plant habit of this new cultivar, 'SAVapam', is upright and vigorous with uniform branching, reaching 26 to 32 inches in height and width. The length of the flowering stem varies from 4¼- to 6-inches. The distance between nodes varies from 23/32- to 28/32-inch on the central portion of the stem, between five- and seven-leaflet leaves, with 24/32-inch being the most common spacing. There are usually five to seven mature, five- and/or seven-leaflet leaves per stem and usually three, alternately located, three-leaflet leaves just below the peduncle on a flowering stem and one three-leaflet leaf at the base of the stem. (Stems branching off from candelabra-type growth may have very erratic spacing between nodes and up to 1½-inches apart with 1¼-inches being the most common spacing.)

'SAVapam' has above average resistance to blackspot and rust and very good resistance to powdery and downy mildews. Its resistance to aphids is slightly below average but it has very good resistance to thrip, mites and rose midge. This cultivar has been tested for hardiness to zone 5 and for heat tolerance to zone 9.

Foliage: Mature foliage is pinnately compound. five- or seven-leaflet leaves. Size is average for cultivars in the miniflora class, 3½- to 3¾-inches long. Terminal leaflets are usually around 1 9/16- to 1¾-inches long and ⅞-inch wide. The shape of the leaflets is oval, pointed, having an acute tip and obtuse base. The upper surface is semi-glossy and the reverse is matte. The central vein and primary lateral veins protrude slightly on the underside of the leaflets with the primary lateral veins being nearly parallel. Both surfaces are glabrous. Margins are doubly serrated with a stipitate gland at the tip of each serration.

New foliage: is a dark green flushed with red anthocyanin coloring, near 187A and the coloring sometimes appearing even darker. The reverse is near 187A.

Old foliage: Anthocyanin color is absent on the old foliage. The upper surface is dark green, near 139A, and the under surface is slightly lighter green, near 137B.

Color of the petioles: and petiolules on the young foliage is a red, near 183A, on the ridge on the adaxial side and the remainder is lighter green, near 145A. On mature foliage, the color on the adaxial side is near 146D and flushed with near 183C and the reverse is also near 146D and also flushed except where the stipules are attached.

Petioles/rachis: have a few stipitate glands along the ridges, a random hair in the grooves, and numerous, straight, upright hairs where petiolules are attached. The under surface has some stipitate glands, on rare occasion in pairs, and random spacing; a few (most often four) prickles; and occasionally stiff hairs. The color of the glands and prickles is oxblood red, near 183C. Petiolules are similar, adding a few stipitate glands in a row along the middle of the underside.

Stipules: are occasionally found at the base of the peduncle as well as on either side of the petiole where it attaches to the stem. Margins are very unevenly serrated, with stipitate glands between each serrate and glands on the tip of each serration. The reverse is glabrous. Part of the edge rolls back, part does not; detached tips point adaxial or abaxial, randomly. The stipules measure 6/16-inch attached to the petiole and 3/16-inch detached to 5/16-inch attached and 2/16-inch detached. Pairs are usually uneven. The color is near 146D with anthocyanin coloring absent. Glands are oxblood red, near 183B.

Wood: Main stalks range from ⅜-inch to ¾ inch diameter and ¾-inch is the most common size. Primary laterals vary in diameter from ⅛ to 3/16-inch; those originating from a main lateral above the ground are most often 3/16-inch. Those originating from below the ground vary from ⅛ to 3/16-inch. The texture of the new wood is glabrous and smooth. The color of the new wood is between 137 B and 147A, a very dark green. Old wood color is lighter, being near 146A and is also glabrous.

Cuttings taken from young growth produce roots in 10 to 14 days, under mist in greenhouse conditions.

Prickles: There are three to six prickles per inch on the main stalks, zero to two prickles per inch on the primary laterals and two to four per inch on the secondary laterals. Location is erratic. The base is elliptical and as long as the prickle; the form is straight. The length of the prickles on the main stalks varies from 6/32-inch to 9/32-inch and on the laterals from 6/32-inch to 11/32-inch; width is 3/32- to 5/32-inch, irrespective of length. The color when young is oxblood red, near 183D and when mature, a grayish-brown, near 199D. Prickles on the undersides of the rachis are three to ten in quantity with four being the quantity most often found.

It is claimed:

1. A new and distinct variety of hardy, miniflora rose plant is claimed, substantially as illustrated and described, with long lasting, old-fashioned, double flowers of pink and pink blend, on a vigorous and well branched plant, having above average disease resistance.

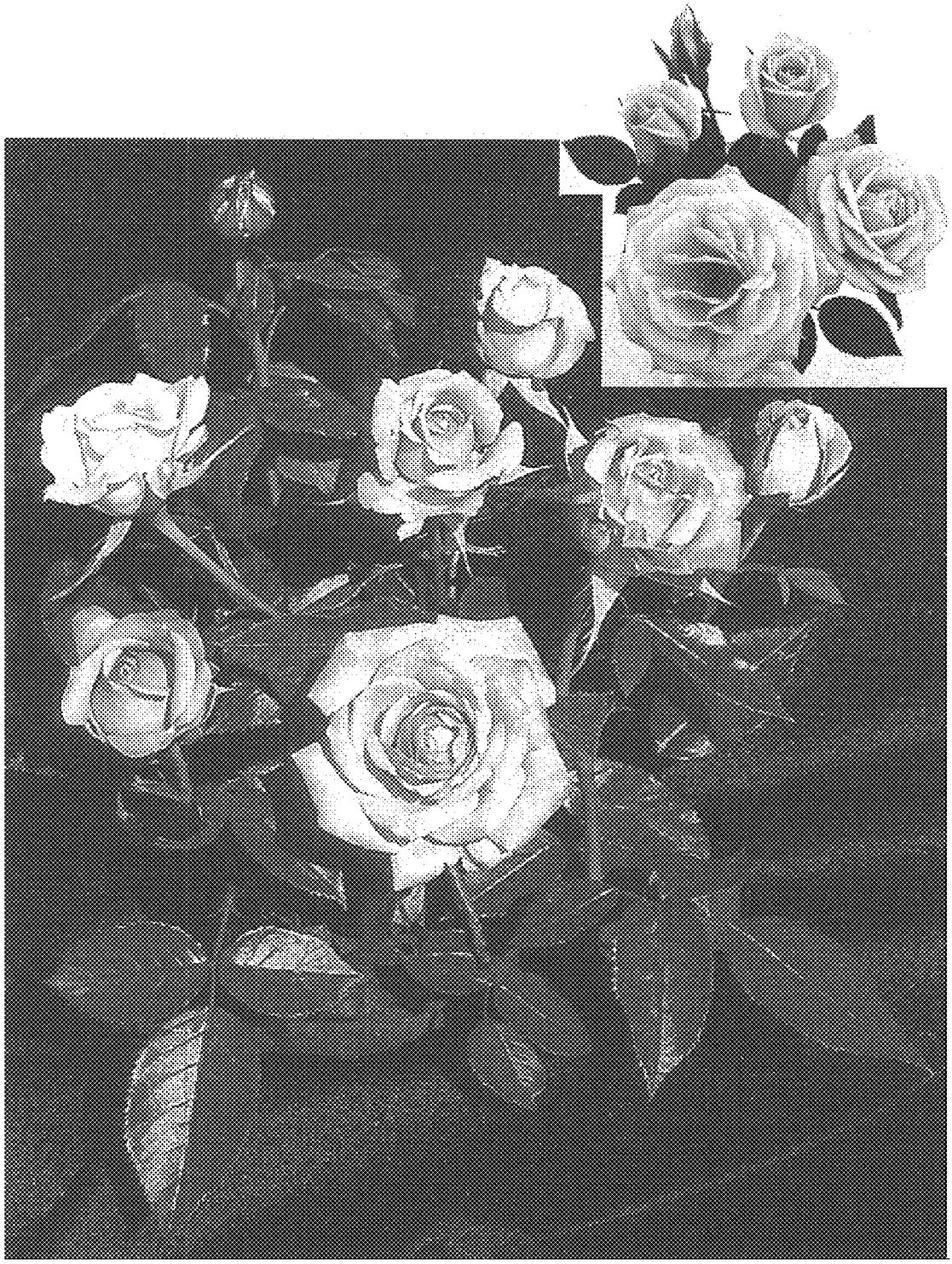

* * * * *